United States Patent
Kinney et al.

(10) Patent No.: US 7,328,549 B2
(45) Date of Patent: Feb. 12, 2008

(54) PROCESS FOR ASEPTIC VACUUM FILLING AND STOPPERING OF LOW VISCOSITY LIQUIDS IN SYRINGES

(75) Inventors: Shawn Kinney, Wayland, MA (US); Andrea Wagner, Wayland, MA (US)

(73) Assignee: Hyaluron, Inc., Burlington, MA (US)

( * ) Notice: Subject to any disclaimer, the term of this patent is extended or adjusted under 35 U.S.C. 154(b) by 0 days.

(21) Appl. No.: 11/657,814

(22) Filed: Jan. 25, 2007

(65) Prior Publication Data

US 2007/0169435 A1    Jul. 26, 2007

Related U.S. Application Data

(63) Continuation of application No. 11/584,914, filed on Oct. 23, 2006.

(60) Provisional application No. 60/798,573, filed on May 8, 2006, provisional application No. 60/762,232, filed on Jan. 26, 2006.

(51) Int. Cl.
 *B65B 31/02* (2006.01)
 *B67B 1/00* (2006.01)

(52) U.S. Cl. .............. 53/432; 53/440; 53/471; 53/489; 53/510; 53/127; 53/281; 53/319; 53/330

(58) Field of Classification Search .......... 53/432, 53/510, 127, 440, 471, 264, 489, 281, 319, 53/330; 141/7, 59, 64
See application file for complete search history.

(56) References Cited

U.S. PATENT DOCUMENTS

| | | | | |
|---|---|---|---|---|
| 2,503,944 A * | 4/1950 | Frascari | ................. | 53/440 |
| 3,020,685 A * | 2/1962 | Kurek | ................. | 53/403 |
| 3,245,194 A * | 4/1966 | Carski | ................. | 53/432 |
| 3,650,084 A * | 3/1972 | Moreland | ................. | 53/471 |
| 3,733,771 A * | 5/1973 | Megowen | ................. | 53/471 |
| 4,623,516 A * | 11/1986 | Weiler et al. | ................. | 422/28 |
| 4,987,726 A * | 1/1991 | Petho et al. | ................. | 53/510 |
| 5,860,461 A * | 1/1999 | Helmut | ................. | 141/326 |
| 5,884,457 A * | 3/1999 | Ortiz et al. | ................. | 53/468 |
| 6,640,842 B1 * | 11/2003 | Laukenmann et al. | ......... | 141/2 |
| 6,688,081 B2 * | 2/2004 | Boyd | ................. | 53/440 |

FOREIGN PATENT DOCUMENTS

DE           19909995 A1 *  9/2000
WO   PCT/US 06/41460      9/2007

OTHER PUBLICATIONS

Inova, Inc. "inoVa H3-FV Vacuum Syringe Filler: Operations Manual." Chapters 3 & 4.
Kwak, et al. "Gas bubble formation in nonequilibrium water-gas solutions", J. Chem Phys 78 (9), p. 5795-5799.
Farrell, et al., "A device for stoppering bottles and ampoules under vacuum or dry nitrogen conditions", J. Clin Pathol. 26(5):381-382.

\* cited by examiner

*Primary Examiner*—Stephen F. Gerrity
(74) *Attorney, Agent, or Firm*—Sonia K. Guterman; Adam M. Schoen; Lawson & Weitzen, LLP

(57) ABSTRACT

A process by which low viscosities liquids are filled into syringes without gas bubbles utilizing lowered temperature and valves to isolate the filling system from the vacuum. The liquid may be drug, device, pharmaceutical, and/or biotech products.

14 Claims, 3 Drawing Sheets

Panel A

Panel B

PROCESS FOR ASEPTIC VACUUM FILLING AND STOPPERING OF LOW VISCOSITY LIQUIDS IN SYRINGES

RELATED APPLICATIONS

The present application claims the benefit of provisional application Ser. No. 60/762,232 filed in the U.S. Patent and Trademark Office on Jan. 26, 2006, provisional application Ser. No. 60/798,573 filed in the U.S. Patent and Trademark Office on May 8, 2006, and utility application Ser. No. 11/584,914 filed in the U.S. Patent and Trademark Office on Oct. 23, 2006 from which this application is a continuation, all of which are hereby incorporated by reference herein in their entirety.

TECHNICAL FIELD

Methods are provided for successful aseptic vacuum filling and stoppering of syringes with low viscosity liquids with no appreciable gas bubble.

BACKGROUND

Equipment and processes are known for aseptic vacuum filling and stoppering of liquids into syringes. Current processes and equipment are capable of vacuum filling and stoppering viscous liquids without a significant gas bubble, however these processes are not suitable for vacuum filling and stoppering of low viscosity liquids with no appreciable gas bubble.

Gas bubbles located inside a syringe expand when the syringe is exposed to a change in gas pressure, such as that experienced at higher elevations. In such circumstances, a plunger will move up the barrel of the syringe until the external pressure is returned to its original level, at which point the plunger will return to its original position. This plunger movement may introduce micro-organisms or other contaminants into the product contained in the syringe. The amount of plunger movement is proportional to the size of the gas bubble inside the syringe and the difference in pressure between the pressure at which the syringe was filled and the ambient pressure to which the syringe is then exposed.

In current processes for vacuum stoppering or vacuum filling of containers with low viscosity liquids, sub optimal vacuum levels have to be applied or only a small percentage of the syringe can be filled (50% or less) due to splashing, out-gassing and boil over of the liquid in the syringe when under vacuum. Viscous liquids can be filled and stoppered under optimal deep vacuum as their viscosities inhibit liquid splashing, out-gassing and boiling. Another difficulty that arises in vacuum filling of low viscosity liquids is controlling fill volume. With low viscosity liquids, the liquid that is in the filling line between the needle outlet and the fill pump outlet is forced out of the line into the syringe by out-gassing of the liquid and expansion of gas bubbles under vacuum. This is not a concern in filling containers with viscous liquids.

Processes that can fill syringes without gas bubbles offer significant benefits to products that are air sensitive, shear sensitive and degraded by liquid gas interfaces (i.e. some proteins). Further, aseptic conditions in syringes in which the plunger (plunger) is free to move in response to external pressure changes are improved by bubble-free filling. There is a need for bubble-free filling that produces a filled container such as a syringe with no gas bubble and that reduces or eliminates plunger movement described above.

SUMMARY

An aspect of the invention provided herein is a process for removing gas bubbles, the process includes filling containers under aseptic conditions with sterile fluid and stoppering the containers, wherein filling and stoppering steps are performed under a vacuum utilizing check valves to isolate fill lines (also called feed lines) and lowered temperature to suppress vapor pressure of the fluid being filled. Lowered temperature is obtained, for example, by cooling product feed into filling pumps, placing an in-line chiller on the filling pumps, placing an in-line chiller on the fill lines, reducing filling room temperature, chilling the containers on-line with a cold gas, or pre-chilling the containers.

In related embodiments, the process further includes, prior to filling the containers, applying a pre-vacuum. In another related embodiment of the process, the gas bubbles are air, for example, air dissolved in a sample of a product. In a further related embodiment, the gas bubbles are a gas other than air, such as a gas with which the sample was purged to remove air.

In still another related embodiment of the process, the containers are selected from at least one of the group of vials, hypodermic syringes, bottles, cartridges, and capsules. In yet another related embodiment of the process, the fluid is a product, for example, a protein, a polymer, a polysaccharide, a vaccine, an anti-serum, a mucoprotein, a nucleic acid, and a lipoprotein. In certain embodiments of the process, the product is recombinantly produced.

In other embodiments of the process, the extent of the vacuum is at least about 27 inches of mercury; for example, the vacuum is at least about 29 inches, or at least about 35 inches, or is at least about 40 inches, or at least about 50 inches of mercury. In a related embodiment the temperature is less than about 8 C, for example less than about 5 C, or less than about 0 C.

In still other various embodiments of the process, the volume of the fluid is about 0.01 ml to about 100 ml, for example, the volume is about 0.01 ml to about 5.0 ml, or is about 1.0 ml to about 50 ml; or is about 5.0 ml to about 100 ml.

In certain embodiments, the process further includes prior to filling, sterilizing the fluid by filter sterilization. In a related embodiment of the process, the filling and stoppering is automated, for example, the automated process is high-throughput.

Another aspect of the invention provided herein is an article of manufacture having a fluid in an aseptically filled and stoppered container prepared by a method of filling the container under aseptic conditions with sterile fluid and stoppering the containers, wherein filling and/or stoppering steps are performed under a vacuum.

In other embodiments of the article of manufacture, the amount of the vacuum is at least about 28 inches of mercury; for example, the vacuum is at least about 29 inches of mercury. In another related embodiment of the article of manufacture, the fluid further includes a pharmaceutically acceptable buffer or salt. In certain related embodiments, the fluid is primarily aqueous.

BRIEF DESCRIPTION OF THE DRAWINGS

FIG. 1 panel B is a photograph of the same syringes as in FIG. 1 panel A, at an external gas pressure of 19" Hg vacuum. A change in pressure resulted in movement of the plunger in each of the middle and the right syringes respectively, compared to the positions of these plungers at normal atmospheric pressure.

DETAILED DESCRIPTION

Figure 1:
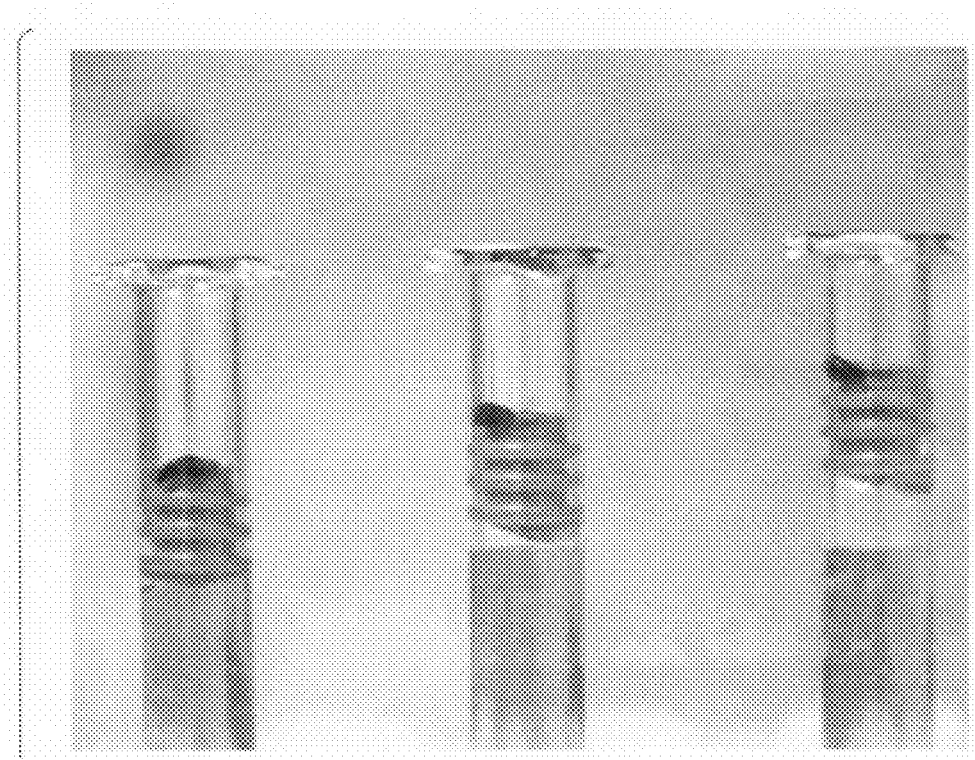
FIG. 1 panel A is a photograph of syringes at normal atmospheric pressure having gas bubbles (middle and right) and a control have no gas bubble.
Figure 1:
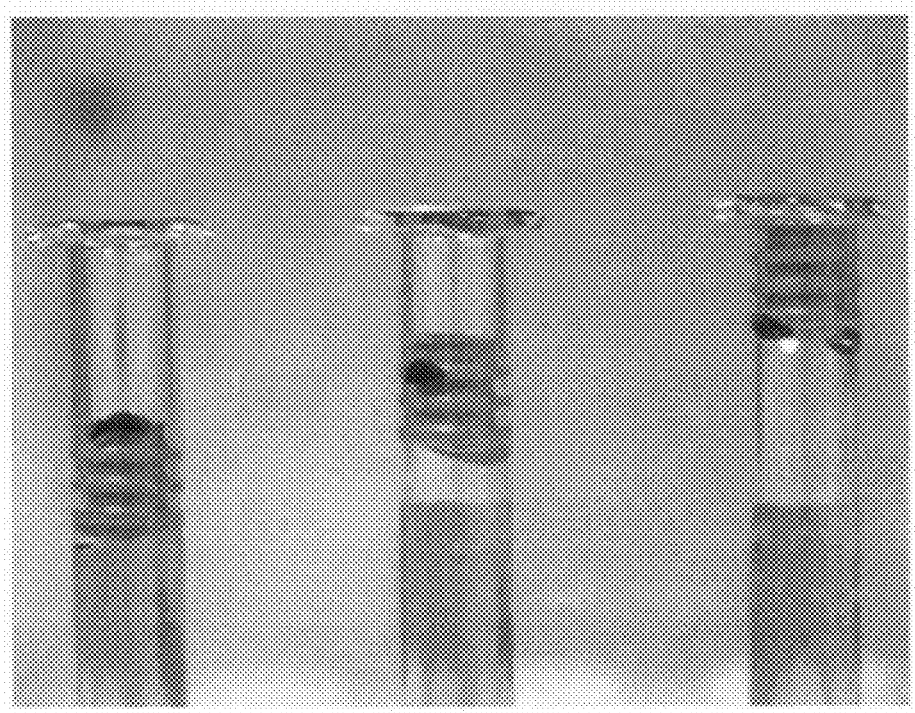

High value materials such as proteins may be sensitive to air, to shear forces generated by motion of a bubble sliding back and forth in a syringe, particularly at the gas-liquid interface that may cause denaturation of the protein, hence decreasing activity and shelf life of the protein in the filled syringe. Some proteins may be prone to aggregation due to the presence of a gas bubble and/or silicon inside the syringe. Other compounds such as epinephrine are sensitive to air, such that removing as much air from the syringe with the product as possible leads to improved product stability and shelf life. Removal of air is preferable to replacement of the air with another gas, for reasons of economy and possibly reactivity. Further, as described above, absence of a gas bubble in the syringe prevents unwanted plunger movement when the syringe is exposed to reduced pressure, thereby reducing or preventing potential microbial contamination.

As used in the specification and in the claims herein, the word "viscosity" means the measure of a resistance to flow, or the thickness or resistance to flow of a fluid. Viscosity is a result of the internal friction of molecules of a material. Viscosity generally decreases as temperature increases.

Viscosity is measured by a unit of absolute, or dynamic viscosity, indicated in centimeter-gram-second, or poise (p). One poise is the viscosity of a fluid that requires a shearing force of one dyne to move a square centimeter area of either of two parallel layers of fluid one centimeter apart with a velocity of one centimeter per second relative to the other layer, the space between the layers being filled with the fluid. One of ordinary skill in the art commonly measures viscosity in centipoise (cps). The phrase "low viscosity" means a fluid with a measured cps of less than about 1500 cps, for example, less than about 1000 cps or less than about 500 cps.

Applicant had found that vacuum stoppering of low viscosity solutions into syringes, especially narrow bore syringes (diameters less than 10 mm) was difficult because a bubble trapped in the syringe tip during the filling process would expand during the application of vacuum and push the liquid out of the syringe. Vacuum filling the same syringe to remove the gas bubble in the tip prior to filling caused excessive boiling, bumping and splashing of the liquid, leading to loss of liquid, and to liquid being caught between the plunger and the wall of the syringe. Additionally, vacuum filling pulled a substantial proportion of the solution out of the fill line back to the filling pump, resulting in irreproducible fill volumes among multiple syringes.

Introducing a valve between the vacuum and the fill line such as a check valve with a 25 psi crack pressure was experimentally observed herein to prevent the liquid from being pulled out of the filling line. Reducing the temperature of the liquid and/or syringe was experimentally observed herein to reduce the boiling and bumping of the liquid. The syringe was then successfully stoppered with no discernable gas bubble.

The Applicant has found that with check valves to isolate the filling lines from the vacuum, and through the use of reduced temperature, syringes were able to be filled in a variety of sizes (in a range from 1 ml through 100 ml), with a variety of volumes appropriate for the range of syringe sizes (volumes of 0.1 ml through 100 ml), in an automated system, the resulting filled syringes having no discernable gas bubble.

In an exemplary embodiment of the process, high vacuum conditions were used in conjunction with an automated filling apparatus, Inova H3-5V (available from Inova, a division of Optima Instruments, Schwäbisch Hall, Germany), using a vacuum level of about 28-29.9 inches of mercury. The automated filling apparatus is used to fill containers under vacuum and after filling, the containers are also sealed with stoppers under vacuum.

A vacuum unit evacuates the filling needles before filling. When the pumping piston moves down, product is drawn via a suction hose and continuous rotation of a piston alternatively opens and closes the suction inlet and pumping outlet on the pump cylinder. During each pump stroke of the piston, filling product is drawn in via a fill hose and then pumped into the container via the filling needle. After vacuum valves have been opened, the remaining gas is drawn out of the containers and the vacuum lines.

When stopper insertion is terminated, the valves of the vacuum line are closed and the vacuum chamber is aerated. Further details are described in a description of the machine prepared by the manufacturer (Inova, a division of Optima Instruments, Schwäbisch Hall, Germany), which is herein incorporated by reference; however, the particular manufacturer and model of the machine are not integral to the process, and any suitable filling apparatus can be adapted to the conditions described herein.

The invention having now been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications cited throughout this application, are hereby incorporated by reference.

EXAMPLES

Example 1

Gas Free Filling of Epinephrine in a Syringe

Epinephrine, an air-sensitive high value product is commercially important and used in high volume for stock piling at hospitals and other medical facilities to test the process herein, was prepared in solution and filled into a 1 ml syringe with an internal diameter of 10 mm. Test syringes were vacuum filled and vacuum stoppered, as described herein with check valves and at reduced temperature.

It was observed that filling and stoppering of test syringes were achieved with no observed gas bubble, at fill volumes ranging from 0.1 ml to 1.0 ml. In contrast, control syringes filled at room temperature and in the absence of check valves displayed gas bubbles and inconsistent fill volumes. It was further observed in the test syringes that no product was caught between the plunger and the syringe wall.

This process of filling with no resulting gas bubble is envisioned to increase the shelf life of this air sensitive drug in a syringe filled by the process, during storage, and to improve consistency of the fill volumes, resulting in benefits to the manufacturer and to the end user patients.

Example 2

Prevention of Plunger Movement in Syringe when Exposed to Reduced Ambient Pressure Vacuum stoppering of low viscosity solutions into syringes, especially narrow bore syringes (diameters less than 10 mm), was limited by presence of a gas bubble trapped in the syringe tip during the filling process because the bubble expands during the application of vacuum and pushes the liquid out of the syringe.

This limitation and the advantages of the process is shown herein by the following test. Syringes having plungers were filled with a low viscosity aqueous fluid at normal pressure, as shown in FIG. 1 panel A. One syringe was filled by the procedure of Example 1 resulting in a syringe filled with fluid and no gas bubble (FIG. 1 panel A, left syringe). Two other syringes were filled by a different process, resulting in moderate sized and large sized gas bubbles respectively, as shown in FIG. 1 panel A middle and right syringe respectively. The location of the top of the plunger was noted on the syringe with a marker.

A vacuum of approximately 19" Hg was applied to these syringes as shown in FIG. 1 panel B. The plunger in the syringe filled by the procedure of Example 1, resulting in a syringe filled with fluid and no gas bubble. The plunger was observed not to move from its original position when the vacuum was applied, as shown in FIG. 1 panel B left syringe. The plungers in the two syringes containing a gas bubble each moved a significant amount, as shown in FIG. 1 panel B middle and right syringes. The observed amount of plunger movement was in proportion to the size of the gas bubble observed prior to applying vacuum.

Example 3

Inhibition of Growth of Control Microbe *Bacillus Subtilis*

Absence of a gas bubble in the syringe was found to prevent unwanted plunger movement when the syringe was exposed to reduced pressure. Further experiments were designed to test the effects of the process on reducing or preventing potential microbial contamination.

Figure 2:
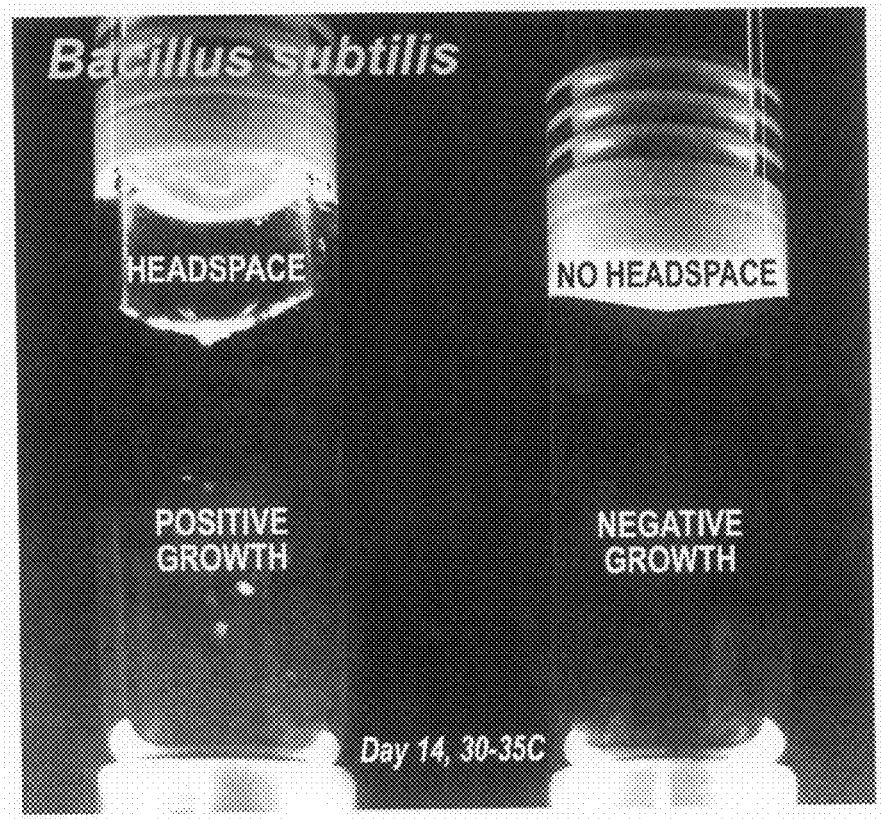
FIG. 2 is a photograph of vials containing bacterial growth medium inoculated with Bacillus subtilis and incubated for two weeks. The vial on the right was filled by a process of the present invention resulting in no headspace (no gas bubble) in the vial; the vial on the left was filled by a different process resulting in headspace (presence of a gas bubble) in the vial. The vial on the left shows growth of B. subtilis (indicated in the photograph as "positive growth") compared to the vial on the right showing cleared medium, indicated in the photograph as "negative growth".

A trypticase soy broth solution that supports microbial growth was prepared and an inoculum of the Gram positive bacterium *B. subtilis* was added to the medium. The medium containing the *B. subtilis* was filled into vials. A portion of the vials were filled using the process of the present invention. No headspace (no gas bubble) was observed in an exemplary vial, as shown in FIG. 2, right vial. Control vials were filled using a different method. Production of a large headspace (presence of a gas bubble) was observed in the control vials, as shown in FIG. 2, left vial. The vials containing the medium with *B. subtilis* were incubated at 20-25° C. for one week and then 30-35° C. for a second week.

After two weeks of incubation, the vials were visually observed for detection of growth of *B. subtilis*. Vials having headspace showed positive growth of *B. subtilis*, as shown in FIG. 2, left vial, indicated in the photograph as "positive growth". Vials filled by methods herein were found to have been filled with no headspace. Following incubation, the *B. subtilis* cells were found to have lysed, due to the absence of air for this obligate aerobic organism, resulting in clear medium, as shown in FIG. 2 right vial, indicated in the photograph as "negative growth".

Since the process of the present invention filled the vial without the introduction of any gas, *B. subtilis*, a microbe which requires oxygen to survive, could not grow. In contrast, the other filling process introduced a gas into the vial which sustained *B. subtilis* and allowed this microbe to grow. Therefore, the process of the present invention provides an advantage over prior art filling processes by filling vials without introducing any gas bubbles.

Example 4

Inhibition of Growth of Control Microbe *Candida Albicans*

Figure 3:
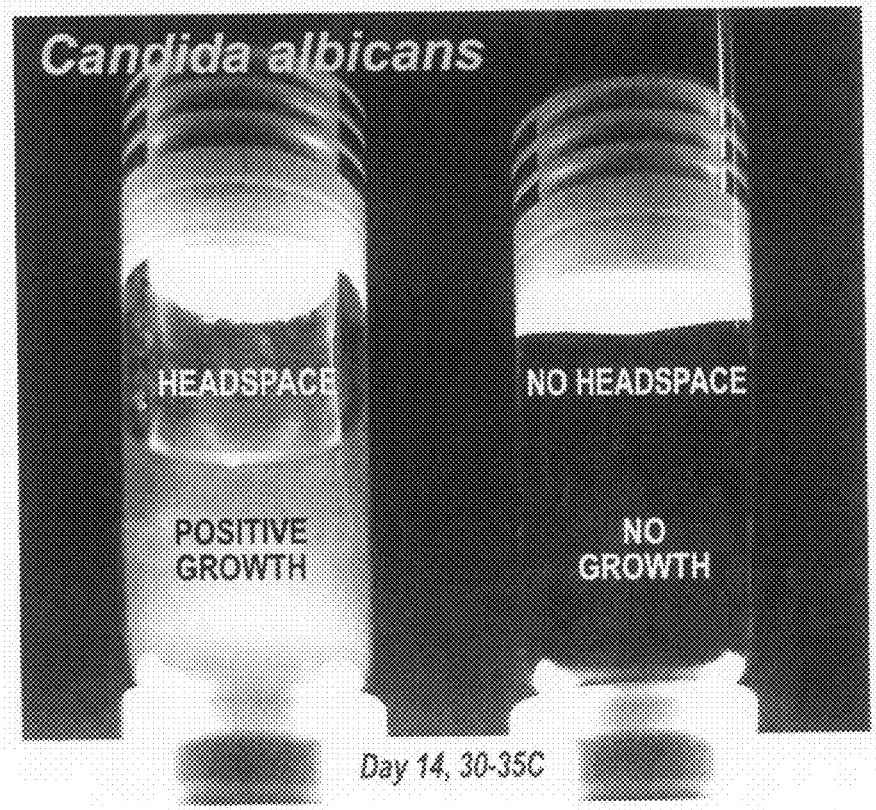
FIG. 3 is a photograph of vials containing bacterial growth medium inoculated with Candida albicans and incubated for two weeks. The vial on the right was filled by the process of the present invention resulting in no headspace (no gas bubble) in the vial; the vial on the left was filled by a different process resulting in headspace (presence of a gas bubble) in the vial. The vial on the left shows growth of C. albicans (indicated in the photograph as "positive growth") compared to the vial on the right showing no growth (indicated in the photograph as "no growth").

A trypticase soy broth solution that supports microbial growth was prepared and an inoculum of a yeast species, *C. albicans*, was added to the medium. The medium containing the *C. albicans* was filled into vials. A portion of the vials were filled using the process of the present invention. No headspace (no gas bubble) was observed in an exemplary vial, as shown in FIG. 3, right vial. Control vials were filled using a different method. Production of a large headspace (presence of a gas bubble) was observed in the control vials, as shown in FIG. 3, left vial. The vials containing the medium with *C. albicans* were incubated at 20-25° C. for one week and then 30-35° C. for a second week.

After two weeks of incubation, the vials were visually observed for detection of growth of *C. albicans*. Vials having headspace showed positive growth of *C. albicans*, as shown in FIG. 3, left vial, indicated in the photograph as "positive growth". Vials filled by methods herein were found to have been filled with no headspace. Following incubation, the *C. albicans* cells were found to have showed no *Candida albicans* growth as shown in FIG. 3 right vial, indicated in the photograph as "no growth".

Example 5

Inhibition of Growth of Control Microbe *Aspergillus Niger*

Figure 4:
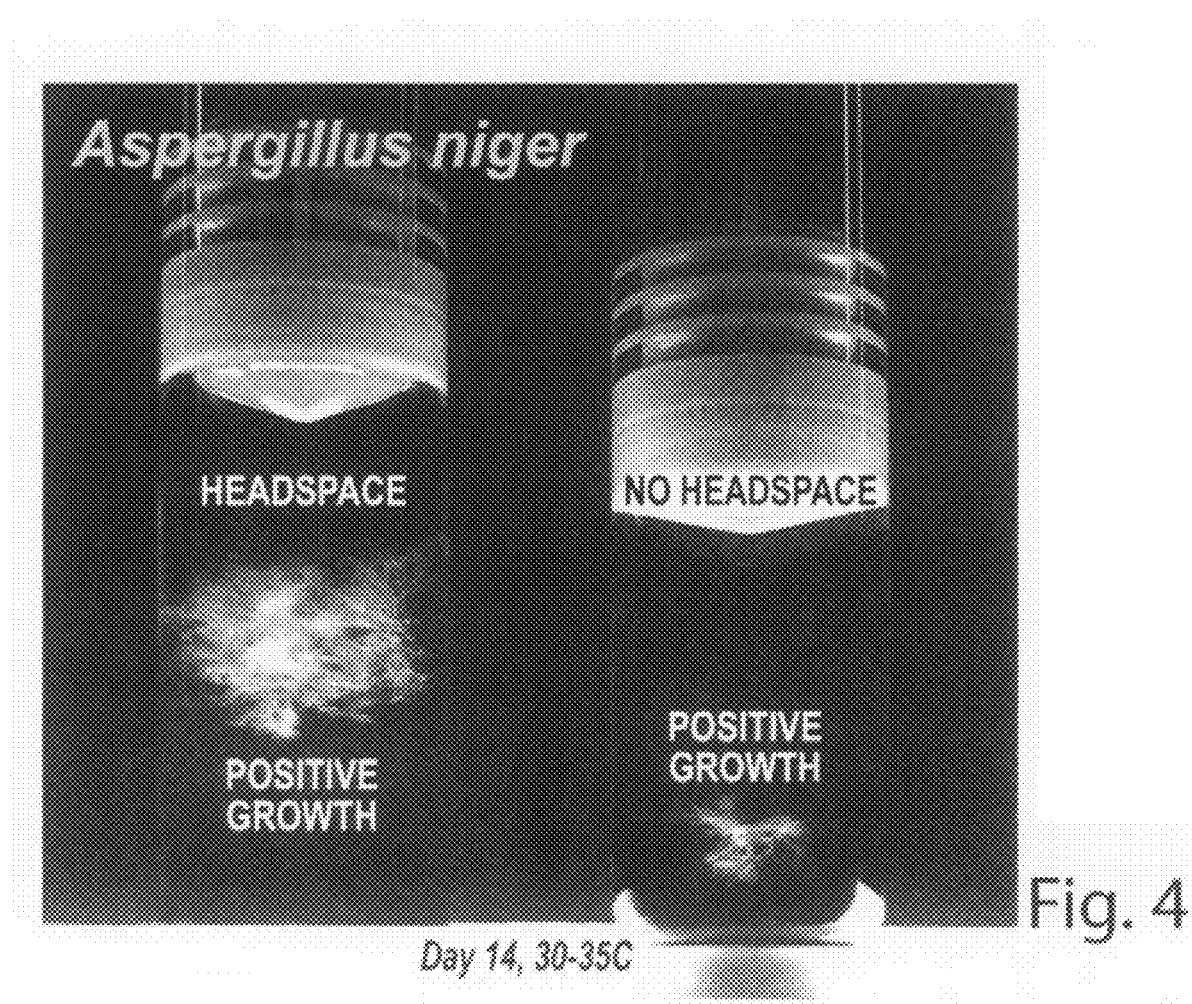
FIG. 4 is a photograph of vials containing bacterial growth medium inoculated with Aspergillus niger and incubated for two weeks. The vial on the right was filled by the process of the present invention resulting in no headspace (no gas bubble) in the vial; the vial on the left was filled by a different process resulting in headspace (presence of a gas bubble) in the vial. The vial on the left shows significant growth of A. niger (indicated in the photograph as "positive growth") compared to the vial on the right showing significantly less growth of A. niger (indicated in the photograph as "positive growth").

A trypticase soy broth solution that supports microbial growth was prepared and an inoculum of hyphal fungus, *A. niger*, was added to the medium. The medium containing the *A. niger* was filled into vials. A portion of the vials were filled using the process of the present invention. No headspace (no gas bubble) was observed in an exemplary vial, as shown in FIG. 4, right vial. Control vials were filled using a different method. Production of a large headspace (presence of a gas bubble) was observed in the control vials, as shown in FIG. 4, left vial. The vials containing the medium with *A. niger* were incubated at 20-25° C. for one week and then 30-35° C. for a second week.

After two weeks of incubation, the vials were visually observed for detection of growth of *A. niger*. Vials having headspace showed significant positive growth of *A. niger*, as shown in FIG. 4, left vial, indicated in the photograph as "positive growth". Vials filled by methods herein were found to have been filled with no headspace. Following incubation, the *A. niger* cells were found to have shown significantly less growth of *A. niger* compared to the control vials, as shown in FIG. 4, right vial indicated in the photograph as "positive growth". The growth of *A. niger* in the vial without headspace was an order of magnitude less compared to the growth of *A. niger* in the vial having headspace, as shown in FIG. 4 left and right vials.

What is claimed is:

1. A process for removing gas bubbles from a low viscosity fluid, the process comprising filling containers under aseptic conditions with a sterile, low viscosity fluid; and stoppering the containers, wherein filling and stoppering steps are performed in a vacuum chamber under a vacuum utilizing check valves to isolate fill lines, and lowered temperature to suppress vapor pressure of the low viscosity fluid being filled.

2. The process according to claim 1, wherein the lowered temperature is obtained by a procedure selected from at least one of, cooling product feed into filling pumps, placing an in-line chiller on the filling pumps, placing an in-line chiller on the fill lines, reducing filling room temperature, chilling the containers on-line with a cold gas, and pre-chilling the containers.

3. The process according to claim 1, further comprising, prior to filling the containers, applying a pre-vacuum.

4. The process according to claim 1, wherein the gas bubbles comprise air.

5. The process according to claim 1, wherein the gas bubbles comprise a gas other than air.

6. The process according to claim 1, wherein the extent of the vacuum is at least about 28 inches of mercury and the temperature is less than about 8 C.

7. The process according to claim 1, wherein the extent of the vacuum is at least about 29 inches of mercury and the temperature is less than about 8 C.

8. The process according to claim 1, wherein the volume of the fluid is about 0.01 ml to about 100 ml.

9. The process according to claim 1, further comprising prior to filling, sterilizing the fluid by filter sterilization.

10. The process according to claim 1, wherein the filling and stoppering is automated.

11. The process according to claim 10, wherein the automated process is high-throughput.

12. The process according to claim 1, wherein the containers are selected from at least one of the group of vials, hypodermic syringes, bottles, cartridges, and capsules.

13. The process according to claim 1, wherein the fluid comprises a product selected from at least one of a protein, polymer, a polysaccharide, a vaccine, an anti-serum, a mucoprotein, a nucleic acid, and a lipoprotein.

14. The process according to claim 13, wherein the product is recombinantly produced.

* * * * *